United States Patent [19]

Wattanasin

[11] Patent Number: 5,753,675
[45] Date of Patent: May 19, 1998

[54] QUINOLINE ANALOGS OF MEVALONOLACTONE AND DERIVATIVES THEREOF

[75] Inventor: Sompong Wattanasin, Hopatcong, N.J.

[73] Assignee: Novartis Pharmaceuticals Corporation, East Hanover, N.J.

[21] Appl. No.: 498,301

[22] Filed: Mar. 23, 1990

Related U.S. Application Data

[63] Continuation of Ser. No. 318,773, Mar. 3, 1989, abandoned.

[51] Int. Cl.$^6$ .......... A61K 31/47; C07D 401/04; C07D 405/04
[52] U.S. Cl. .......... 514/311; 514/314; 546/167; 546/171; 546/173; 546/174; 546/175
[58] Field of Search .......... 514/311, 314; 546/167, 171, 173, 174, 175

[56] References Cited

U.S. PATENT DOCUMENTS 4,761,419  8/1988  Picard et al. .......... 546/156
5,011,930  4/1991  Fujikawa et al. .......... 514/311

FOREIGN PATENT DOCUMENTS 304063  2/1986  European Pat. Off. .......... 546/156

*Primary Examiner*—Johann Richter
*Assistant Examiner*—Taofiq Solola
*Attorney, Agent, or Firm*—Diane E. Furman

[57] ABSTRACT

Quinoline analogs of mevalonolactone of the following formula are useful as anti-cholesterol synthesis agents:

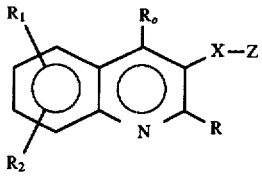

where the substituents are as defined in the specification.

10 Claims, No Drawings

QUINOLINE ANALOGS OF MEVALONOLACTONE AND DERIVATIVES THEREOF

This application is a continuation of Ser. No. 07/318,773 filed Mar. 3, 1989, now abandoned.

This invention relates to compounds of the formula

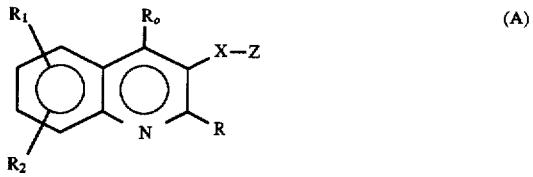

(A)

wherein each of R and $R_o$ is, independently $C_{1-6}$alkyl (primary, secondary or tertiary), $C_{3-7}$cycloalkyl or ring A

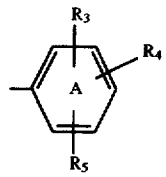

each of $R_1$, $R_2$, $R_3$, $R_4$ and $R_5$ is, independently hydrogen, $C_{1-4}$alkyl, $C_{1-4}$alkoxy, trifluoromethyl, fluoro, chloro, phenoxy, benzyloxy or hydroxy; with the provisos that not more than one of $R_1$ and $R_2$ is trifluoromethyl, not more than one of $R_1$ and $R_2$ is phenoxy, not more than one of $R_1$ and $R_2$ is benzyloxy, not more than one of $R_1$ and $R_2$ is hydroxy, not more than one of $R_3$–$R_5$ is the trifluoromethyl, not more than one of $R_3$–$R_5$ is phenoxy, not more than one of $R_3$–$R_5$ is benzyloxy and not more than one of $R_3$–$R_5$ is hydroxy;

X is —(CH$_2$)$_2$— or —CH=CH— (cis and/or trans);

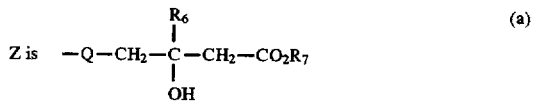

(a)

or

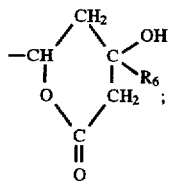

(b)

wherein Q is —C— or —CH—
            ‖       |
            O       OH with the proviso that Q may be

only when X is —CH=CH— and/or $R_6$ is $C_{1-3}$alkyl;

$R_6$ is hydrogen or $C_{1-3}$alkyl;

$R_7$ is hydrogen, $R_8$ or M;

$R_8$ is a physiologically acceptable and hydrolyzable ester group; and

M is a pharmaceutically acceptable cation.

The term "pharmaceutically acceptable and hydrolyzable ester group" means a group which, together with the —COO— radical to which it is attached, forms an ester group which is physiologically acceptable and hydrolyzable under physiological conditions to yield a compound of Formula A wherein $R_7$ is hydrogen and an alcohol which itself physiologically acceptable, i.e. non-toxic at the desired dosage level, and which, preferably, is free of centers of asymmetry. Examples of such groups are $C_{1-3}$alkyl, n-butyl, i-butyl, t-butyl, and benzyl, collectively referred to as $R_{8a}$.

Compounds of this invention may conveniently be categorized into two groups, depending on the value of Z. Compounds where Z is

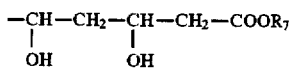

will be referred to as compounds of Formula I. Compounds where Z is

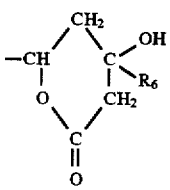

will be referred to as compounds of Formula II.

The compounds of the present invention have two centers of asymmetry (the two carbon atoms bearing the hydroxy groups when Z is (a), and the carbon atom bearing the hydroxy group and the carbon atom having the free valence when Z is (b) provided that $R_7$ is free of centers of asymmetry). Thus there are four stereoisomeric forms (enantiomers) of each compound (two racemates or pairs of diastereoisomers). The four stereoisomers may be designated as the R,R, R,S, S,R, and S,S enantiomers, all four stereoisomers being within the scope of this invention. When $R_7$ contains one or more centers of asymmetry, there are eight or more stereoisomers. When Q is

—CH—,
 |
 OH

then each compound has one center of asymmetry (the carbon atom bearing the hydroxy group and $R_6$), and therefore, there are two enantiomers of each compound, provided that $R_7$ does not contain any center of asymmetry. The two stereoisomers may be designated as the 3R and 3S isomers. If $R_7$ contains one or more centers of asymmetry, then there are four or more centers of asymmetry.

As between otherwise identical compounds of Formula A, those where the Z group is a) are generally preferred over those where the Z group is b). For compounds where Z is a), the erythro isomers are generally preferred over the threo isomers, erythro and threo referring to the relative positions of the hydroxy groups in the 3- and 5-positions of the group a). When Z is b), the trans lactones are generally preferred over the cis lactones, cis and trans referring to the relative positions of $R_6$ and the hydrogen atom in the 6-position of the group b) (adjacent to the O in the ring).

The preferred stereoisomers of the compounds having only two centers of asymmetry wherein X is —CH=CH— and Z is a) are the 3R, 5S and 3R,5R isomers and the racemate of which each is a constituent, i.e. the 3R,5S-3S,5R (erythro) and 3R,5R-3S,5S (threo) racemates, with the 3R,5S isomer and the racemate of which it is a constituent being more preferred and the 3R,5S isomer being most preferred.

The preferred stereoisomers of the compounds of Formula I having only two centers of asymmetry wherein X is b) are the 4R,6R and 4R,6S isomers and the racemate of which each is a constituent, i.e., the 4R,6R-4S,6S (trans lactone) and the 4R,6S-4S,6R (cis lactone) racemates, with the 4R,6R isomer and the racemate of which it is a constituent being more preferred and the 4R,6R isomer being most preferred.

These preferences also apply to compounds having more than two centers of asymmetry and represent the preferred configurations of the indicated positions.

Preferred compounds of this invention are the following.

$R_1$ and $R_2$ are preferably hydrogen;

one of R and $R_o$ is preferably $C_{1-6}$alkyl, more preferably isopropyl or methyl, and the other is preferably Ring A, more preferably phenyl, 4-fluorophenyl or 3,5-dimethylphenyl; most preferably R is the alkyl group and $R_o$ is Ring A;

X is preferably —CH=CH—, most preferably (E) —CH=CH—;

Z is preferably (a) wherein Q is

or (b), most preferably the former.

Q is preferably

$R_6$ is preferably hydrogen;

$R_7$ is preferably hydrogen, M or $C_{1-2}$alkyl; most preferably M or $C_{1-2}$alkyl;

$R_8$ is preferably methyl or ethyl;

M is preferably $Na^+$, $K^+$ or $NH_4^+$, most preferably $Na^+$.

Specific compounds of Formula I may be prepared according to the following preferred Reaction Scheme A. It should be noted in the following Reaction Schemes, that if any compound of Formula A contains a hydroxy group as $R_1$–$R_5$, then the hydroxy group should be protected by e.g. a diphenyl-t-butyl silyl group (in compounds of formula III–XI and XIV–XVI). The group is cleaved at the end of the synthesis by Reaction B-4 (detailed below).

REACTION SCHEME A

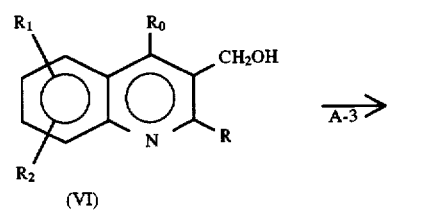

(III) + (IV) → (V)

-continued
REACTION SCHEME A

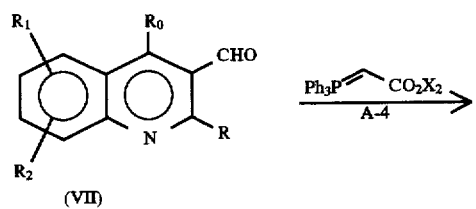

(VI)

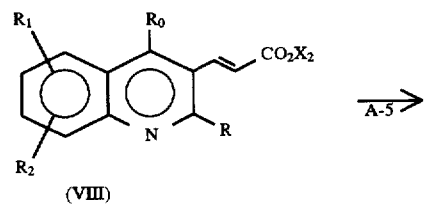

(VII)

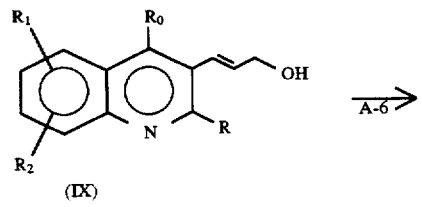

(VIII)

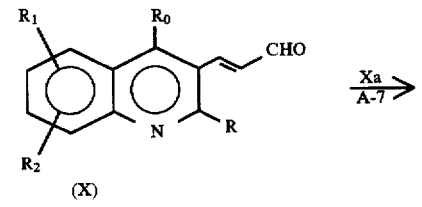

(IX)

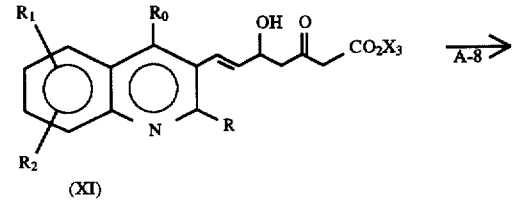

(X)

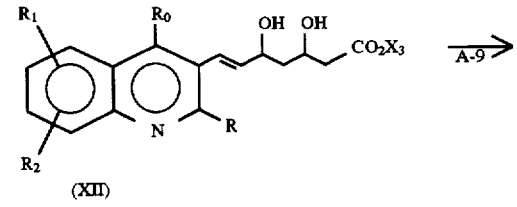

(XI)

(XII)

-continued
REACTION SCHEME A

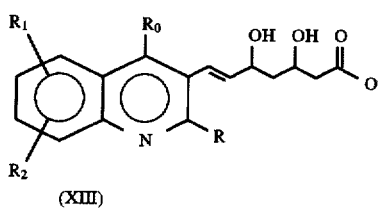

(XIII)

Starting material III can be obtained by methods described by Morrison and Mulholland, 1958, *J. Chem. Soc.* p. 2702, which is hereby incorporated by reference. Next, V is reduced to give VI. This reaction has also been described by Fehnel, 1968. *J. Heterocyclic Chem* 4:565, which is also hereby incorporated by reference. In Step A-3, VI is oxidized to VII. Step A-4 is a Wittig reaction producing VIII. Compound VIII is then reduced to IX. In Step A-6, IX is oxidized to X. The aldehyde X is then reacted with an acetoacetate in Step A-7 to give XI. Compound XI is reduced to give XII. Next, in Step A-9, XII is hydrolyzed to the salt form XIII.

Compounds of both Formula I and II may be made according to Reaction Scheme B. Starting material for Reaction Scheme B is Compound VI from Reaction Scheme A.

REACTION SCHEME B

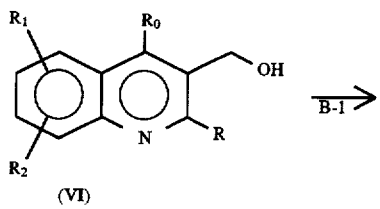

(VI)

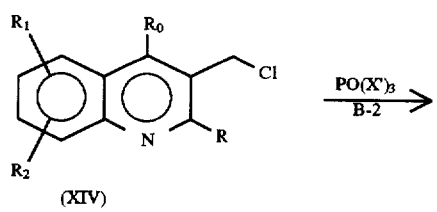

(XIV)

-continued
REACTION SCHEME B

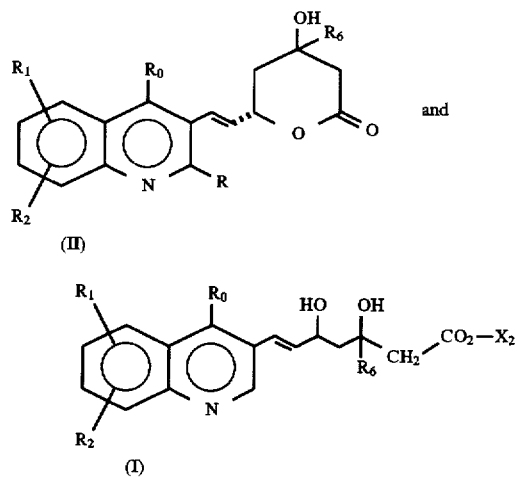

Step B-1 is a chlorination of Compound IV to yield XIV. Next, the phosphonate (XV) is made. In Step B-3, a coupling reaction forms Compound XVI. This product is then deprotected in Step B-4 to yield Compounds of Formulae I and II.

REACTION SCHEME C

Compounds of formula A wherein X is —(CH$_2$)$_2$— and Z is (a) where R$_6$ is hydrogen may be synthesized by the following reactions:

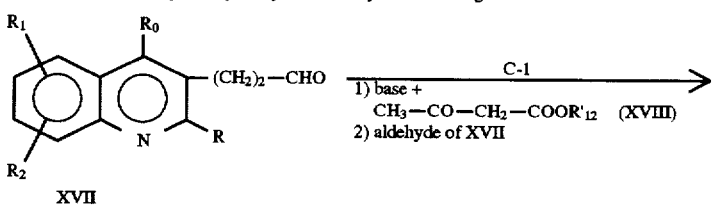

XVII

-continued
REACTION SCHEME C
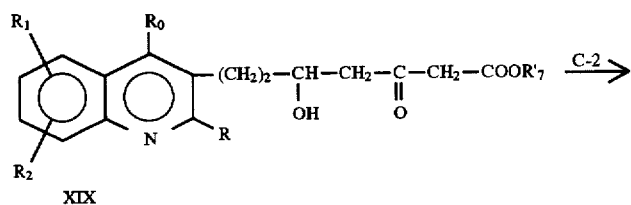
XIX
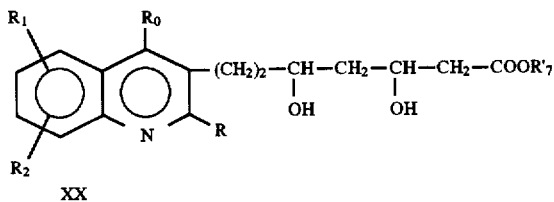
XX
REACTION SCHEME D
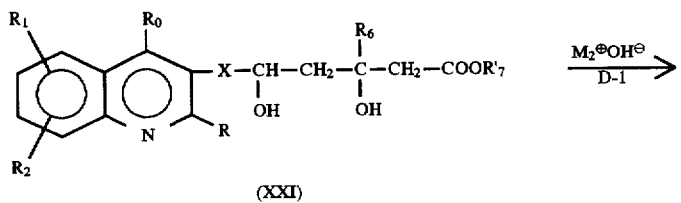
(XXI)
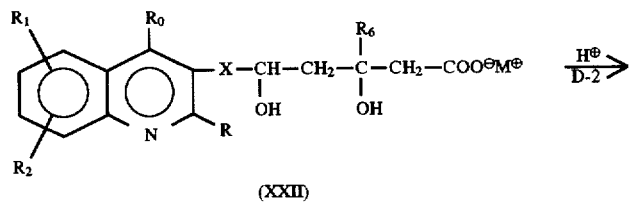
(XXII)
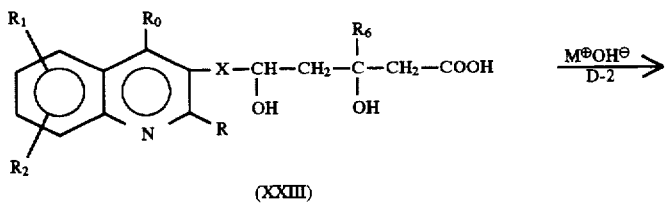
(XXIII)
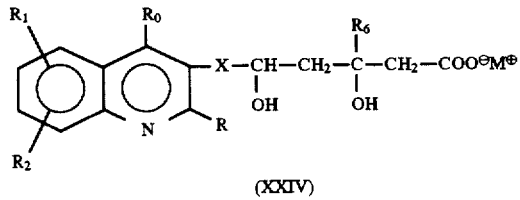
(XXIV)

-continued
REACTION SCHEME D
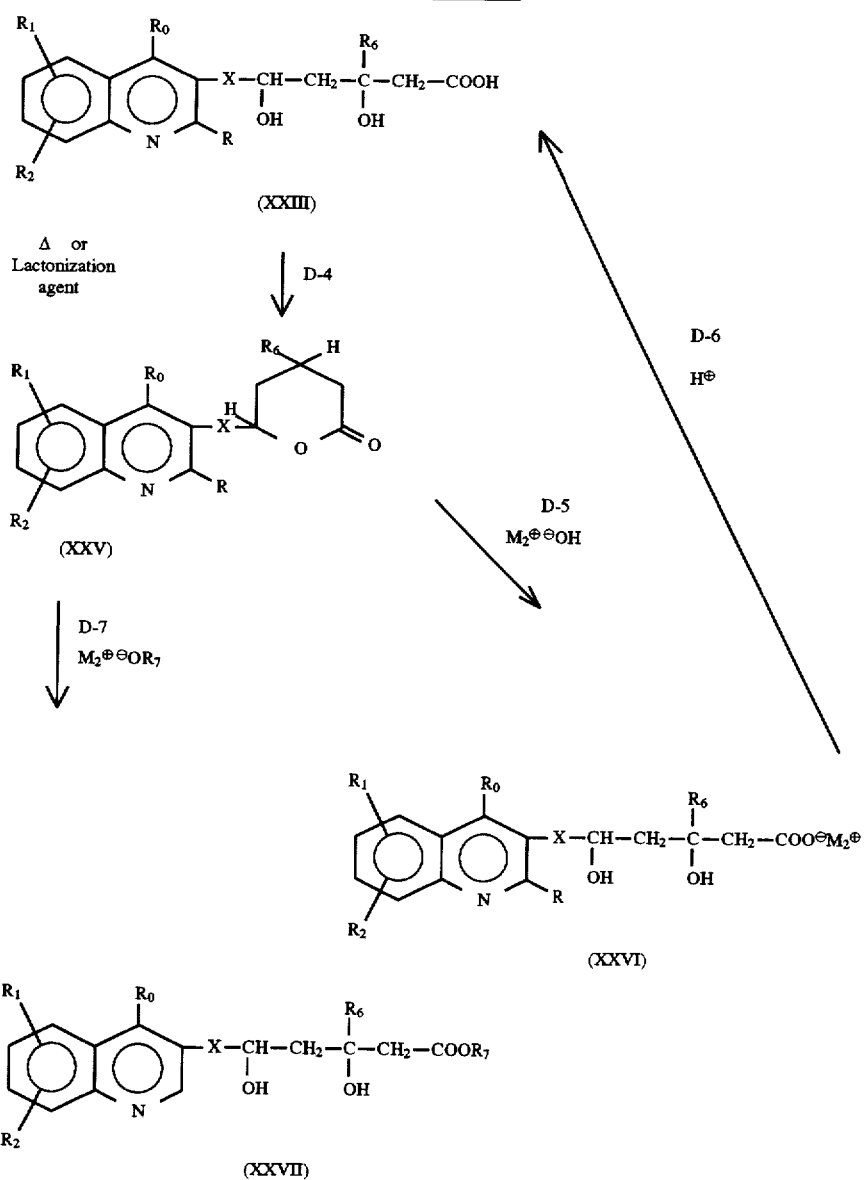
REACTION SCHEME E
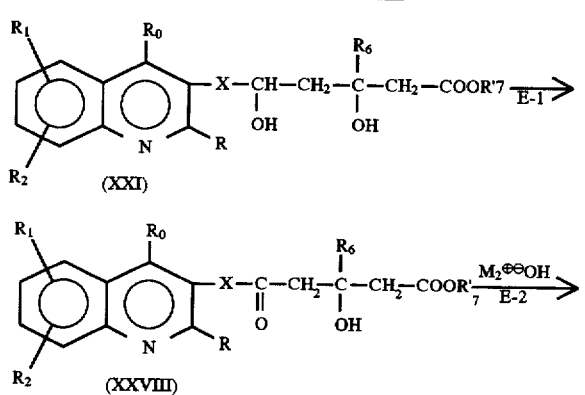
-continued
REACTION SCHEME E
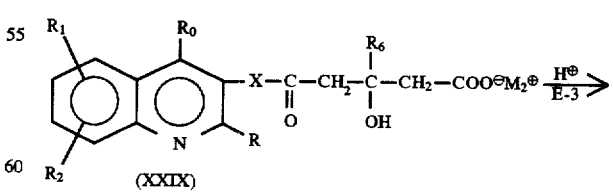

-continued
REACTION SCHEME E

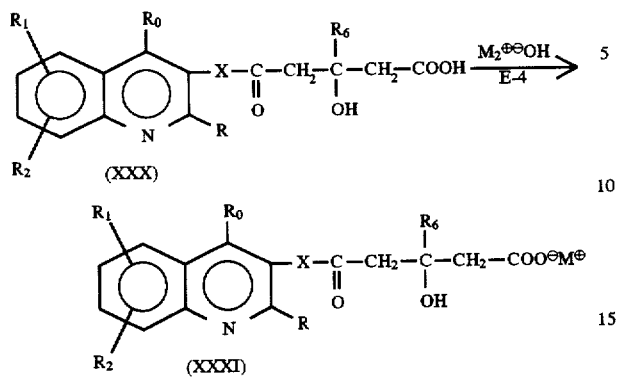

In the foregoing reaction schemes,

X₁ may be any alkyl group, especially $C_{1-2}$alkyl;

X₂ may be $C_{1-3}$ alkyl, n-butyl, i-butyl, t-butyl or benzyl;

X₃ may be any alkyl group, preferably X₂ and most preferably $C_{1-2}$alkyl;

X' may be ethyl or methyl;

X_a is an acetoacetate, alkyl or benzyl ester, preferably ethyl acetoacetate; and R₆ may be as defined above.

R'₇ is $C_{1-3}$alkyl, n-butyl, i-butyl, t-butyl or benzyl, more preferably $C_{1-3}$alkyl, and most preferably $C_{1-2}$alkyl, especially ethyl.

Particular reaction conditions for Reaction Schemes A and B are presented below. In this table, the following abbreviations are used:

AIO=anhydrous inert organic solvent

ES=ether solvent, for example, diethyl ether, 1,2-diethoxyethane, 1,2-dimethoxyethane, tetrahydrofuran and mixtures thereof esp.=especially HC=hydrocarbon solvent, for example, benzene, toluene, xylene and mixtures thereof HLA=halogenated lower alkane solvent, for example, carbon tetrachloride, chloroform, 1,1-dichloroethane, 1,2-dichloroethane, methylene chloride and 1,1,2-trichloroethane, usually preferably methylene chloride hr. (hrs.)=hour(s)

IO=inert organic solvent min.=minutes pref.=preferably, preferred

THF=tetrahydrofuran

Compounds of high optical purity are obtainable by a multi-step procedure involving carrying out a Wittig reaction between a 1) 3R,5S-dihydroxy-diprotected aldehyde of the formula W1:

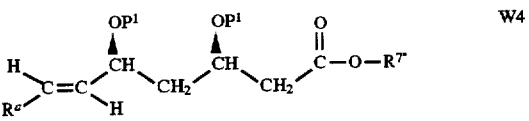

in which $R^{7''}$ is a $C_{1-3}$ alkyl, n-butyl, i-butyl, t-butyl or benzyl, preferably methyl or ethyl, and P' is a protective group, i.e. a trisubstituted silyl radical in which the substituents are bulky groups, e.g. aryl or tertiary-aryl, such as diphenyl-tert.-butyl-silyl, and 2) a Wittig reagent of the formula W2 or W3:

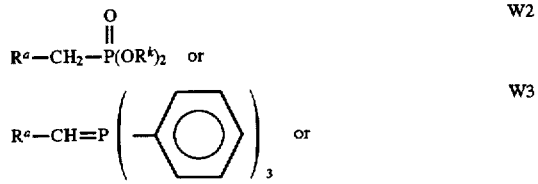

where $R^a$ is a quinolinyl moiety of the formula

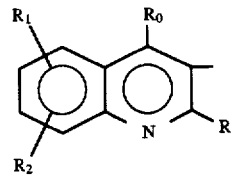

where $R_a$, $R_o$, $R_1$ and $R_2$ are as defined above and $R^k$ is methyl or ethyl, to obtain a corresponding intermediate of the formula W4:

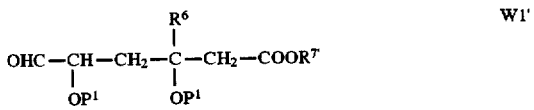

in which $R^a$, $R^{7''}$, and $P^1$ are as defined above; and deprotecting the resulting compound W4 to obtain the corresponding quinoline.

The process may also be employed to obtain all the compounds of Formula I where Q is

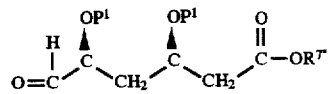

and X is —CH═CH— by reacting appropriate compounds of the formula W1':

OHC—CH—CH₂—C—CH₂—COOR⁷'
         |         |
         OP¹       OP¹
                   R⁶ with a reagent of formula W2 or W3. The former has a tendency to give the trans olefin exclusively although some cis olefin may be obtained, whereas the latter gives a mixture of cis and trans olefins, but predominantly the trans olefin. Compounds of the formula W1' are disclosed in U.S. Pat. No. 4,613,610. The obtained olefinic compounds may be hydrogenated analogously to the hydrogenation reactions of said patent to obtain the corresponding compounds of Formula I where X is —CH₂—CH₂—.

Most of the molar amounts (ratios) given in the following table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the following table are merely exemplary, and it is within the ability of one of ordinary skill in the art to vary those that are not critical.

The reaction times set forth in the following table are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the table.

As utilized in the following table, the term "solvent" embraces mixtures of solvents and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "inert atmosphere", as utilized in the following table, means an atmosphere that does not react with any of the reactants, intermediates or end products or otherwise interfere with the reaction. While a carbon dioxide atmosphere is suitable for certain reactions, the inert atmosphere is usually dry nitrogen, helium, neon, argon or krypton, or a mixture thereof, and most often dry nitrogen, to maintain anhydrous conditions. Most reactions, including those where the use of an inert atmosphere is not specified, are carried out under an inert atmosphere, usually dry nitrogen, for convenience.

In the preceding table, n-butyllithium is preferably employed as a 1.3–1.7M. solution in hexane, and lithium diisopropylamide is preferably prepared in situ from n-butyllithium and diisoipropylamine.

| Reaction Step | Reagents, Molar Ratios and Comments | Temperature | Time | Solvent | Inert Atmosphere |
|---|---|---|---|---|---|
| A-1 Condensation with a β-Keto ester | EtOH<br>$X_1$ is any alkyl group<br>1–1.2 moles IV per mole III | 80–100° C. | 1–5 hrs. | Lower alkanol, pref. ethanol | Yes |
| A-2 reduction | Strong metal hydride reducing agent, e.g. lithium aluminum hydride or diiso-butylaluminum hydride; at least 2 equivalents, pref. 2.5–5 equivalents, of transferable hydride per mole V, e.g. at least 0.5 mole, pref. 1–1.25 moles, lithium aluminum hydride or at least 2 moles, pref. 2.5–5 moles diisobutylaluminum hydride per mole V. | 20 to −80° C. | 0.3–4 hrs. | AIO, pref. ES, eg. THF, or diethyl ether, HLA, esp. methylene chloride or mixture of HLA and toluene | Yes |
| A-3 oxidation | 5–50 moles, pref. 7–25 moles manganese dioxide (pref. activated) per mole VI | 20°–120° C., pref. 110° | 2–72 hrs., pref. 3–5 hrs. | IO, pref. HLA, esp. methylene chloride or HC, esp. toluene | — |
| A-4 Wittig | 1–1.3 moles $Ph_3P{=}CH{-}COOX_2$, preferably $Ph_3P{=}CH{-}COOCH_3$, per VII | 50° C.-reflux, pref. 60°–115° C., esp. 90°–115° C. | 3–8 hrs., pref. 4–8 hrs. | AIO, pref. E.S. THF, or HC esp. toluene | Yes<br>Yes |
| A-5 Reduction | Same as A-2 | | | | |
| A-6 Oxidation | 5–50 moles, pref. 7–25 moles manganese dioxide (pref. activated) per mole IX | 20°–80° C., pref. pref. 20°–25° C. | 2–72 hrs., pref. 12–48 hrs. | IO, pref. HLA, esp. methylene chloride or HC, esp. toluene | — |
| A-7 | 1) Generation of dianion of Xa; 1 mole Xa and 2–2.2 equivalents strong base, pref. 1–1.1 moles sodium hydride then 1–1.1 moles n-butyl-lithium or 2–2.2 moles lithium di-isopropylamide. | −50°–10° C., pref. −30°–5° C. | 0.3–1.5 hrs. | AIO, e.g., ES, pref. THF | Yes |
| | 2) 1–2.5 moles, pref. 1.2–2.2 moles, more pref. 1.3–2.0 moles, of dianion of Xa (assuming 100% conversion of Xa to its dianion) per mole X. Product (XI) is racemic. | −80°–0° C., pref. −60°–0° C., more pref. −30°–−10° C. | 0–3–4 hrs., pref. 0.3–2 hrs. | Same as Step 1 | Yes |
| | 3) Quench with, for example, ammonium chloride solution or 1N. hydrochloric acid | −80–25° C. | 1–5 min. | Same as Step 1 | — |
| A-8 | a) Non-stereoselective: 1–4, pref. 2–4, equivalents of transferable hydride per mole XI, pref. sodium borohydride or complex of t-butylamine and borane. When a racemic XI is utilized, product XII is a mixture of all four possible stereoisomers (the erythro and threo racemates) wherein the ratio of the erythro stereoisomers to the threo stereoisomers ranges from 3:2 to 2:3. | −10°–30° C. | 1–8 hrs. | IO, e.g., lower alkanol, esp. ethanol | yes |
| | b)1) 1–1.3 moles, pref. 1.02–1.3 moles, tri-(primary or secondary $C_{2-4}$ alkyl)borane, pref. triethylborane, and, pref., 0.3–8 liters, e.g., 0.75–6.5 liters, air (at 25° C. and 760 mm. Hg.) per mole XI | 0°–50° C., pref. 0°–25° C. | 0.5–6 hrs., pref. 1–3.5 hrs. | AIO, pref. ES, esp, THF, or pref., mixture of THF and methanol, more pref. 3–4:1 mixture | Yes |
| A-8 (Reduction) (Cont'd) | 2) 0.4–3.5 moles, pref; 1.5–2.5 moles, sodium borohydride per mole IX. After the reaction, quench the reaction mixture with, for example, 1N. hydro- | −100°–−40° C., pref. −100°–−70° C. | 2–48 hrs., pref. 16–48 hrs. | Same as Step 1 | Yes |

-continued

| Reaction Step | Reagents, Molar Ratios and Comments | Temperature | Time | Solvent | Inert Atmosphere |
|---|---|---|---|---|---|
| | chloric acid at −78°−−20° C. and isolate the crude product by extracting with a suitable inert organic solvent (e.g., diethyl ether) and evaporating the solvent at reduced pressure. It is pref. to crystallize the cyclic boron ester, if possible. If the reaction mixture is quenched with water instead of acid, product of this step may be a mixture containing the boron ester and a compound of Formula XXII. 3) large excess of anhydrous methanol, e.g., 50–500 moles per mole IX, or a mixture of methanol (e.g., 10–20 l. per mole IX), hydrogen peroxide (e.g., 4–8 l. of 30% aqueous hydrogen peroxide per mole IX), and a pH 7–7.2 aqueous phosphate buffer (pref. 6–10 l. of a pH 7 aqueous phosphate buffer (e.g., 0.054 M. sodium, 0.024 M. potassium and 0.047 M. phosphate) per mole IX). The amount of buffer must be sufficient to maintain a pH of 7–7.2. Dissolve product of Step 2 in methanol and add buffer and aqueous hydrogen peroxide. See Narasaka et al., Tetrahedron 40, 2233–2238 (1984). | 20°–40° C. pref. 20°–25° C., with methanol alone and −30°–25° C., pref. −10°–10° C., with a mixture of methanol, hydrogen peroxide and buffer | 0.7–60 hrs., pref. 4–60 hrs., with methanol alone and 0.5–2 hrs. with a mixture of methanol, hydrogen peroxide and buffer | Neat | — |
| A-9 Hydrolysis | 0.95–1.05 equivalent, pref. 0.96–0.98 equivalent NaOH per mole XII when XIII is the desired end product | 0°–75° C., pref. 20°–25° C. | 0.5–3 hrs. | Inert aqueous organic eg. mixture of water and lower alkanol, pref. a mixture of water and methanol or esp. ethanol | — |
| B-1 Haolgenation | 1–2 moles, pref. 1.3–1.8 moles of SOCl$_2$ per mole VI | −10°–80° C. | 2–18 hrs. | AIO, pref. ES, eg. diethyl ether or THF, HLA, eg. methylene chloride or HC, e.g. benzene | — |
| B-2 | a) 1–1.1 moles PO(X')$_3$ e.g. P(OEt)$_3$ per mole XIV. Can use excess P(OEt$_3$) as solvent. b) Phosphenium variation | 20°–140° C., usually 100°–140° C. | 6–24 hrs., usually 10–16 hrs. | HC, eg. benzene toluene, or xylene or neat (excess is solvent) P(OEt$_3$) | Yes |
| B-3 Coupling reaction | 1) 1–1.2 moles strong base, pref. n-butyl lithium or lithium diiso-propylamide per mole XV. | −78–0° C. | 10–90 min. | THF | |
| | 2) 1–1.2 moles aldehyde per mole XV | −78–0° C. | 10–90 min. | THF | |
| | 3) Quenched with, e.g. acetic acid | −78–25° C. | 1–5 min. | — | |
| B-4 deprotection | 2–15 moles, pref. 4–10 moles, fluoride reagent, esp. tetra-n-butylammonium fluoride, per mole XVI and 0.5–2 moles, pref. 1.0–1.5 moles glacial acetic acid per mole fluoride reagent | 20–60° C. | 2–120 hrs. | AIO, e.g. ES, pref. THF or mixture of ES, pref. THF, and acetonitrile | |
| C-1 | 1) Generation of dianon of XVII: 1 mole XVIII and 2–2.2 equivalents strong base, pref. 1–1.1 moles sodium hydride then 1–1.1 moles n-butyllithium or 2–2.2 moles lithium diisopropylamide. | −50° C.–10° C., pref. −30–5° C. | 0.3–1.5 hours | AIO, e.g. ES, pref. THF | Yes |
| | 2) 1–2.5 moles, pref. 1.2–2.2 moles, more pref. 1.3–2.0 moles of dianion of XVIII (assuming 100% conversion of XVIII to its dianion) per mole of XVII. Product XIX is racemic. | −80°–0° C., pref. −60°–0° C., more pref. −30–−10° C. | 0.3–4 hrs. pref. 0.3–2 hours | Same as Step 1 | Yes |
| | 3) Quench with, e.g. ammonium chloride solution or 1N HCl. | −80°–25° C. | 1–5 min. | Same as Step 1 | — |
| C-2 Reduction | a) non-stereoselective: 1–4, pref. 2–4 equivalents of transferable hydride per mole XIX, pref. sodium borohydride or complex of t-butylamine and borane. When racemic XIX is used, XX is a mixture of all four stereoisomers, with ratio of erythro to threo stereoisomers ranging from 3:2 to 2:3. b) Stereoselective: 1) 1–1.3 moles, pref. 1.02–1.3 moles, tri (primary or secondary C$_{2-4}$alkyl)-borane, pref. triethylborane, and pref. 0.3–8 liters, eg. 0.75–6.5 liters, air | −10–30° C. | 1–8 hours | IO, eg. lower alkanol esp ethanol | Yes |

-continued

| Reaction Step | Reagents, Molar Ratios and Comments | Temperature | Time | Solvent | Inert Atmosphere |
|---|---|---|---|---|---|
| C (Reduction) (continued) | (at 25° C. and 760 mm Hg) per mole XIX. 2) 0.4–3.5 moles, pref. 1.5–2.5 moles, sodium borohydride per mole XIX. After the reaction, quench the reaction mixture with, for example, 1N. hydrochloric acid at −78°−−20° C. and isolate the crude product by extracting with a suitable inert organic solvent. (e.g., diethyl ether) and evaporating the solvent at reduced pressure. It is pref. to crystallize the cyclic boron ester, if possible. | −100°−−40°C., pref. −100°− −70° C. | 2–48 hours, pref. 16– 48 hours. | Same as Step 1 | Yes |
| | 3) large excess of anhydrous methanol, e.g., 50–500 moles per mole XIX, or a mixture of methanol (e.g., 10–20 l. per mole XIX), hydrogen peroxide (e.g., 4–8 l. of 30 aqueous hydrogen peroxide per mole XIX), and a pH 7–7.2 aqueous phosphate buffer (pref. 6–10 l. of a pH 7 aqueous phosphate buffer (e.g., 0.054 M. sodium, 0.024 M. potassium and 0.047 M. phosphate) per mole XIX). The amount of buffer must be sufficient to maintain a pH of 7–7.2 Dissolve product of Step 2 in methanol and add buffer and aqueous hydrogen peroxide. See Narasaka et al., Tetrahedron 40, 2233–2238 (1984). | 20°–40° C., pref. 20°–25° C., with methanol alone and −30°− 25° C., pref. −10–10° C., with a mixture of methanol, hydrogen peroxide and buffer | 0.7–60 hrs., pref. 4–60 hrs., with methanol alone and 0.5–2 hrs. with a mixture of methanol, hydrogen peroxide and buffer | Neat | — |
| C (Reduction) (Cont'd) | c) Alternative Stereoselective: 1) 1–5 moles zinc borohydride (pref. as 0.1–0.2 M. solution in anhydrous diethyl ether produced as described in Gensler et al., J. Am. Chem. Soc. 82, 6074–6081 (1960)) per mole XIX. | −80°−−50° C., pref. −80°− −70° C. | 0.5–5 hrs., pref. 1–4 hrs. | AIO, pref. ES, esp. diethyl ether or mixture of diethyl ether with another ES | Yes |
| | 2) Add excess methanol (e.g., 10–100 moles per mole IX) and allow to slowly warm to 20°–25° C. | −80°−−50° C., pref. −80°− −70° C.,→ 20°– 20° C. | 1–2 hrs, | Same as Step 1 | — |
| | 3) Add excess dilute aqueous acetic acid to quench the reaction mixture. Can also add the dilute acetic acid at −80°−−50° C. and then allow to warm to 20°–25° C. When a racemic IX is utilized in Alternative b or c, product (XII) is a mixture of the four possible stereoisomers wherein the ratio of the erythro isomers (racemate) to the threo isomers (racemate) is about 4–20:1, usually 5–15:1, except as noted below. Repeated recrystallization of the cyclic boron ester produced in Step 2 of Alternative b, if a solid, may raise the ratio or even yield pure erythro racemate and mother liquors enriched with threo racemate. When, however, the solvent in Step 1 of Alternative b is a mixture of THF and methanol, said ratio may be as high as 50–100:1. | 20°–25° C. | — | Same as Step 1 | — |
| D-1 hydrolysis | 1–1.3 equivalents of M₂OH per mole XXI or if it is desired to isolate XXII, 0.95– 0.995 equivalent M₂OH per mole XXI. | 0° C.-reflux, pref. 0–75° C., esp. 0–25° C. | 0.5–4 hrs. | Inert aqueous organic, e.g. mixture of water and lower alkanol, pref. water and methanol methanol, or esp. ethanol. | — |
| D-2 acidification | At least 1 equivalent, e.g. 1–1.25 equivalents, acid e.g. 2N HCl per mole XXII. | 0–25° C. | 1–5 min. | Water or mixture of water and water missible inert organic solvent e.g. methanol, ethanol, diethyl ether or THF. | — |
| D-3 Neutralization) | 0.95–0.99 equivalent, pref. 0.96–0.98 equivalent, M⊕OH⊖ per mole XXIII. | 0°–25° C., pref. 20–25° C. | 2–10 min. | Same as D-1. | — |
| D-4 (Lactonization) | a) Use of catalytic amount of a strong acid such as p-toluenesulfonic acid monohydrate is optional but usually omit. Use of Dean-Stark trap is pref. if | 75° C.-reflux, pref. 75°– 150° C., esp. 80°–120° C. | 3–18 hrs., pref. 4–7 hrs. | AIO, pref. HC, e.g., benzene, toluene or or xylene or mixture thereof. | — |

-continued

| Reaction Step | Reagents, Molar Ratios and Comments | Temperature | Time | Solvent | Inert Atmosphere |
|---|---|---|---|---|---|
| | solvent forms azeotrope with water. b) 1–1.5 moles of a lactonization agent, e.g., a carbodiimide, pref. a water-soluble carbodiimide such as N-cyclohexyl-N'-[2'-(N''-methylmorpholinium)-ethyl]-carbodiimide p-toluenesulfonate, per mole XXIII. Alternative b often results in higher yields of XXV than Alternative a. Racemic erythro XXIII yields racemic trans (lactone) XXV, racemic threo XXIII yields racemic cis (lactone) XXV, mixture of racemic erythro and threo XXIII yields mixture of racemic trans and cis (lactones) XXV, and single enantiomer of XXIII yields single enantiomer of XXV, e.g., 3R,5S erythro XXIII yields 4R,6S trans XXV. | 10°–35° C., pref. 20°–25° C. | 2–8 hrs., pref. 3–4 hours. | AIO, pref. HLA, esp. methylene chloride. | — |
| D-5 (Hydrolysis) | 1–1.3 equivalents $M_2^{\oplus\ominus}OH$ per mole XXV or, if it is desired to isolate XXVI, 0.94–1 equivalent, preferably 0.97–0.99 equivalent $M_2^{\oplus}OH^{\ominus}$ per mole XXV. Racemic trans (lactone) XXV yields racemic erythro XXVI, racemic cis (lactone) XXV yields racemic threo XXVI, mixture of racemic trans and cis (lactones) XXV yields mixture of racemic erythro and threo XXVI, and single enantiomer of XXV yields single enantiomer of XXVI, e.g., 4R,6S trans XXV yields 3R,5S erythro XXVI. | 0° C.–reflux, pref. 0°–75° C., more pref. 20°–75° C. | 0.5–6 hrs., pref. 1–4 hours | Same as D-3 | — |
| D-6 acidification | Same as D-2. | 0–25° C. | 1–5 min. | Water or mixture of water and water missible inert organic solvent e.g. methanol, ethanol, diethyl ether or THF | — |
| D-7 (Esterification) | At least 2 moles, e.g., 2–10 moles, pref. 2.05–2.5 moles, $M_2^{\oplus}OR_7$ per mole XXV. Racemic trans (lactone) XXV yields racemic erythro XXVII, racemic cis (lactone) XXV yields racemic threo XXVIII, mixture of racemic trans and cis (lactones) XXV yields mixture of racemic erythro and threo XXII, and single enantiomer of XXV yields single enantiomer of XXVII, e.g., 4R,6S trans XXV yields 3R,5S erythro XXVII. | 0°–70° C., pref. 0°–25° C. when $R_7$ is primary alkyl | 1–12 hrs., pref. 1–3 hrs. when $R_7$ is primary alkyl | AIO, e.g., ES such as THF or alcohol of the formula $R_7$—OH ($R_7$ must be same as in $M_2^{\oplus}OR_7^{\ominus}$, if a liquid | — |
| E-1 Oxidation | X is —CH=CH— 5–50 moles manganese dioxide (pref. activated) per mole XXI when X is —(CH$_2$)$_2$: | 20°–80° C., pref. 40°–80° C. | 1–4 days | AIO, pref. ES or HC, esp. toluene | Yes |
| | 1) Prepare Swern's Reagent: 0.9596 l oxalyl chloride and 1.561 l dimethyl sulfoxide per mole XXI to be used in Step 2. | −20–0° C. | 5–15 min. | neat | Yes |
| | 2) Swern's reagent from Step 1 and 6.969 l triethylamine per mole XXI. | −60 to −40° C., pref. −50° C. | 1–6 hrs. | methylene chloride | Yes |
| E-2 Hydrolysis | 1–1.3 equivalents $M_2^{\oplus\ominus}OH$ per mole XXVIII, or if it is desired to isolate XXIX, 0.95–0.995 equivalent $M_2^{\oplus\ominus}OH$ per mole XXVIII | 0° C. to reflux, pref. 0–75° C. esp. 0–25° C. | 0.5–4 hrs. | Inert aqueous organic, e.g. mixture of water and lower alkanol, pref. mixture of water and methanol or esp. ethanol | — |
| E-3 Acidification | At least 1 equivalent, e.g. 1–1.25 equivalents, acid, e.g. 2N HCl per mole XXIX. | 0–25° C. | 1–5 min. | Water or mixture of water and water-miscible inert organic solvent e.g. methanol, ethanol, diethyl ether or THF. | — |
| E-4 Neutralization | 0.95–0.99 equivalent, pref. 0.96–0.98 equivalent $M^{\oplus\ominus}OH$ per mole XXX. | 0–25° C., pref. 20–25° C. | 2–10 min. | Inert aqueous organic, e.g. mixture of water and lower alkanol, pref. mixture of water and methanol or esp. ethanol. | — |

UTILITY

The compounds of formulae I and II, ie in lactone, ester, free acid or salt form, exhibit pharmacological activity and are therefore useful as pharmaceuticals, e.g. for therapy.

In particular the compounds show activity in the following tests:

Test A. In Vitro Microsomal Assay of HMG-CoA Reductase Inhibition:

200 μl. aliquots (1.08–1.50 mg./ml.) of rat liver microsomal suspensions, freshly prepared from male Sprague-Dawley rats (150–225 g. body weight), in Buffer A with 10 mmol. dithiothreitol are incubated with 10 μl. of a solution of the test substance in dimethylacetamide and assayed for HMG-CoA reductase activity as described in Ackerman et al., J. Lipid Res. 18, 408–413 (1977). In the assay the microsomes are the source of the HMG-CoA reductase enzyme which catalyzes the reduction of HMG-CoA to mevalonate. The assay employs a chloroform extraction or a Dowex® 1X8 (200–400 mesh, formate form) ion exchange column to separate the product, [$^{14}$C]mevalonolactone, formed by the HMG-CoA reductase reduction of the substrate, [$^{14}$C]HMG-CoA. [$^{3}$H]mevalonolactone is added as an internal reference. Inhibition of HMG-CoA reductase is calculated from the decrease in specific activity ([$^{14}$C/$^{3}$H]mevalonate) of test groups compared to controls.

The following results were obtained by test A:

Product of Example 3C $IC_{50}$=0.41 μmolar.

Product of Example 4 $IC_{50}$=0.53 μmolar.

Compactin $IC_{50}$=1.01 μmolar.

Mevinolin $IC_{50}$=0.14 μmolar.

$IC_{50}$ is the concentration of the test substance in the assay system calculated to produce a 50% inhibition of HMG-CoA reductase activity. The tests are run at concentrations of test substance between 0.05 and 1000 μmolar.

Test B. In Vivo Cholesterol Biosynthesis Inhibition Test: In vivo studies utilize male Wistar Royal Hart rats weighing 150±20 g. which have been kept for 7–10 days on an altered light cycle (6:30 A.M.–6:30 P.M. dark) housed two per cage and fed powdered Purina Rat Chow and water ad libitum. Three hours before the diurnal maximum of cholesterol synthesis at mid-dark, the rats are administered the test substance (e.g., 0.01–20 mg./kg. body weight) dissolved or as a suspension in 0.5% carboxymethyl-cellulose in a volume of 1 ml./100 g. body weight. Controls receive vehicle alone. One hour after receiving the test substance, the rats are injected intraperitoneally with about 25 μCi/100 g. body weight of sodium [1-$^{14}$C]acetate 1–3 mCi/mmol. Two hours after mid-dark, blood samples are obtained under sodium hexobarbital anesthesia, and the serum is separated by centrifugation.

Serum samples are saponified, neutralized, and the 3β-hydroxysterols are precipitated with digitonin basically as described in Sperry et al., J. Biol. Chem. 187, 97 (1950). The [$^{14}$C]digitonides are then counted by liquid scintillation spectrometry. After correcting for efficiencies, the results are calculated in nCi (nanocuries) of 3β-hydroxysterol formed per 100 ml. of serum. Inhibition of 3β-hydroxysterol synthesis is calculated from the reduction in the nCi of 3β-hydroxysterols formed from test groups compared to controls.

The following results were obtained by Test B:

Example 3C $ED_{50}$=0.49 mg/kg.

Example 4 $ED_{50}$=>1.0 mg/kg.

Compactin $ED_{50}$=3.5 mg/kg.

Mevinolin $ED_{50}$=0.41 mg/kg.

The above presented test data indicate that the compounds of Formulae I and II are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates, and, therefore, as hypolipoproteinemic and anti-atherosclerotic agents. For these indications, the exact dosage will of course vary depending upon the compound employed, mode of administration and treatment desired. For the larger primates, e.g. humans, an indicated daily dosage is in the range from about 1 mg to about 500 mg, preferably from about 10 to 80 mg of a compound of formula I conveniently administered, for example, in divided doses 2 to 4 times a day in unit dosage form containing for example from about 0.25 mg to about 250 mg, preferably in unit dosages of from about 0.25 to 25 mg, of the compound or in sustained release form.

The preferred compounds of the invention are the products of Examples 3C and 4.

The compounds of Formulae I and II may be administered in lactone, ester or free acid form or in pharmaceutically acceptable salt form. Such salts may be prepared in conventional manner and exhibit the same order of activity as the free acid form. The present invention also provides a pharmaceutical composition comprising a compound of Formula I or II in any of its forms in association with pharmaceutically acceptable solid or liquid carrier or diluent. Such compositions may be formulated in conventional manner.

The compounds may be administered by any conventional route in particular enterally, preferably orally, e.g., in the form of tablets or capsules, or parenterally, e.g., in the form of injectable solutions or suspensions.

Salts may be prepared in conventional manner from free acids, lactones and esters and vice-versa. Whilst all salts are covered by the invention pharmaceutically acceptable salts especially sodium, potassium and ammonium, particularly sodium salts are preferred.

The following non-limiting Examples illustrate the invention. Thus another aspect of this invention is a method of inhibiting cholesterol biosynthesis comprising administering a cholesterol biosynthesis-reducing amount of the compounds of either formula I or II.

EXAMPLE 1

Preparation of 6-Heptenoic acid, 3,5-dihydroxy-7-[2-(1-methylethyl)-4-phenylquinolin-3-yl]-ethyl ester, (E)-

Step A: Preparation of 3-Quinolinecarboxylic acid, 2-(1-methylethyl)-4-phenyl-ethyl ester

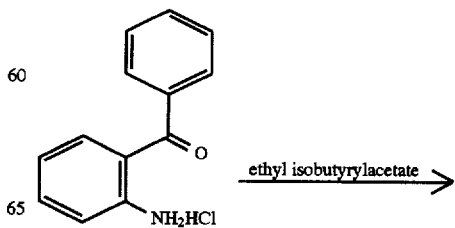

-continued

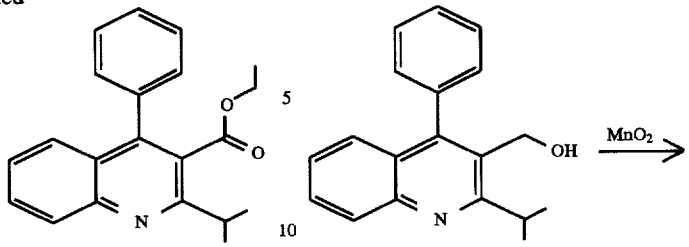

A solution of 11.5 g (0.0493 mole) α-aminobenzophenone hydrochloride and 11.93 ml ethyl isobutyrylacetate (0.07395 mole) in 150 ml abs. ethanol is refluxed for 6 hrs. After the reaction is complete, the solvent is removed under reduced pressure. The residue is basified with NH$_4$OH and product is isolated by extraction with ether. The combined ether extracts are washed with H$_2$O and brine. The organic phase is dried (MgSO$_4$) and concentrated under reduced pressure giving 10.21 g (65%) orange yellow solids.

M.P.: 770°–80°. Anal. Calcd. for C$_{21}$H$_{21}$NO$_2$: C, 78.97; H, 6.63; N, 4.39. Found: C, 78.97; H, 6.63; N, 4.39.

NMR(90 MH$_z$): δ0.9,t,3H; 1.4,d,6H; 3.2,m,1H; 4.0,q,2H; 7.3–7.7,m,8H; 8.2,d,1H.

Step B: Preparation of 3-Quinolinemethanol, 2-(1-methylethyl)-4-phenyl-

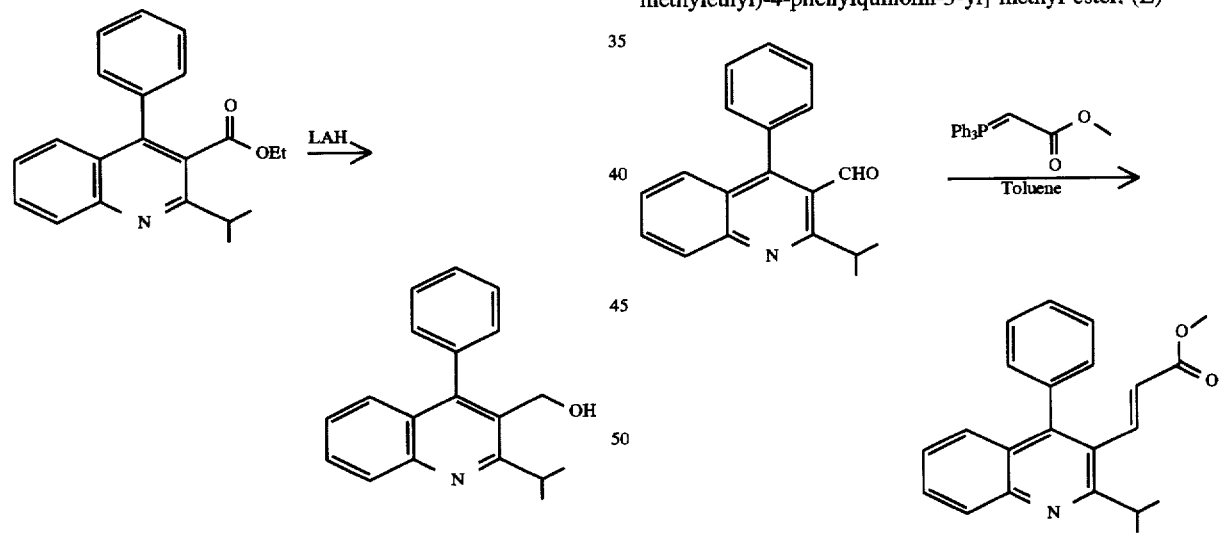

To the solution of 10.21 g (0.03196 mole) quinoline ester in 100 ml anhydrous ether is added 2.43 g (0.063242 mole) LiAlH$_4$ portionwise. After 3 hr. stirring at R.T., the reaction mixture is quenched by pouring it into cold water and is then extracted with ether. The dry ether layer is evaporated in vacuo leaving 8.5 g (96%) of alcohol as yellow solids.

NMR(90 MH$_z$,CDCl$_3$): δ1.0,d,6H; 2.0,m,1H 4.0,s,2H; 4.1,s,1H; 6.3–7.5,m,9H.

Step C: Preparation of 3-Quinolinecarboxaldehyde, 2-(1-methylethyl)-4-phenyl-

A mixture of 8.0 g alcohol from Step B and 16 g of activated manganese dioxide in 150 ml toluene is refluxed for 4 hrs. and is filtered through a pad of silica gel. The evaporation of solvent yields 5.91 g (75%) aldehyde as yellow solids.

The crude product is purified by flash chromatography (elution with 20% ether/pet. ether) M.P.: 82°–85° C. Anal. Calcd. for C$_{19}$H$_{17}$NO: C, 82.88; H, 6.22; N, 5.09; Found: C, 82.48; H, 6.43; N, 4.72. NMR(200 MH$_z$,CDCl$_3$): δ1.35,d, 6H; 4.1,m,1H; 7.3–7.7,m,8H; 8.1,d,1H; 10.0,s,1H.

Step D: Preparation of 2-Propenoic acid, 3-[2-(1-methylethyl)-4-phenylquinolin-3-yl] methyl ester, (E)-

A solution of 5.91 g (0.02149 mole) aldehyde and 8.6 g (0.02578 mole) methyl(triphenyl phosphoranylidene)acetate in 100 ml toluene is refluxed for 1.5 hrs. and is stirred at R.T. overnight. The reaction mixture is diluted with 50% ether/pet. ether and filtered through pad of silica gel. The solvent is removed under reduced pressure. The resulting crystalline residue is triturated with MeOH to give 5.5 g (77.6%) off-white solids.

M.P.: 128°–130° C. Anal. Calcd. for C$_{22}$H$_{21}$NO$_2$: C, 79.73; H, 6.38; N, 4.37; Found: C, 78.74, H, 6.55; N,4.03. NMR(90 MH$_z$,CDCl$_3$): δ1.4,d,6H; 3.5,m,1H; 3.7,s,3H; 5.5–5.75,d,2H; 7.1–7.7,m,8H; 8.1,d,1H.

Step E: Preparation of 2-Propenol, 3-[2-(1-methylethyl)-4-phenylquinolin-3-yl]-(E)-

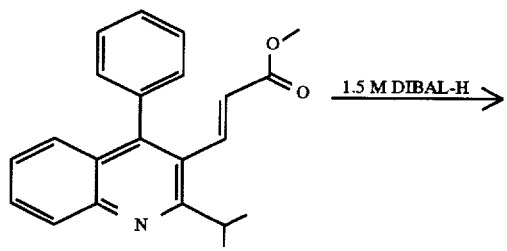

To a cold solution (−78° C.) of 6.25 g (0.01888 mole) α,β-unsaturated ester in 75 ml CH$_2$Cl$_2$ is slowly added 25.2 ml (0.037764 mole) 1.5M diisobutylaluminum hydride in toluene. After the addition is complete, the reaction mixture is stirred at −78° C. for an additional 3 hrs., at which time it is quenched by the addition of 12 ml of 2N NaOH and diluted with ethyl acetate. The mixture is filtered through a pad of silica gel and is washed exhaustively with ethyl acetate. The combined dry organic layers are concentrated in vacuo, yielding 5.42 g crude alcohol as off-white solids. The solids are dissolved in ether and insolubles (aluminum oxides) are filtered. The solvents are evaporated under reduced pressure to give 4.2 g (73.4%) pure alcohol as yellow solids.

M.P.: 119°–121° C. Anal. Calcd. for C$_{21}$H$_{21}$NO: C, 83.13; H, 6.98; N, 4.62. Found: C, 82.05; H, 6.86; N, 3.9. NMR(90 MH$_z$,CDCl$_3$): δ1.4,d,6H; 3.5,m,1H; 4.0,t,2H; 5.3–5.7, pair of t,1H; 6.4–6.6, pair of t,1H; 7.1–7.7,m,8H; 8.1,d,1H.

Step F: Preparation of 2-Propenal, 3-[2-(1-methylethyl)-4-phenylquinolin-3-yl]-(E)-

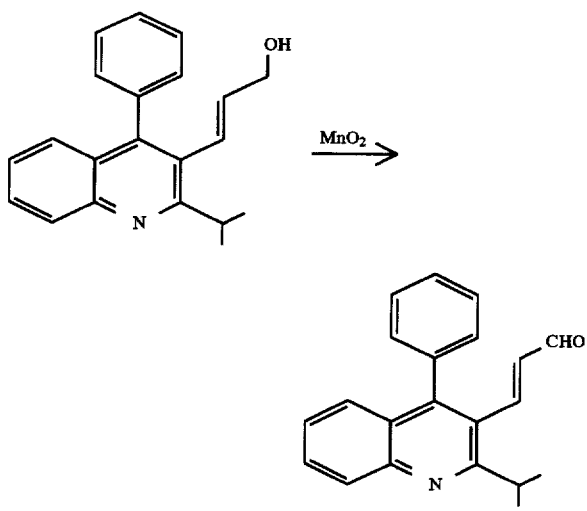

A mixture of 4.0 g (0.0132013 mole) α,β-unsaturated quinoline alcohol and 8.0 g of activated manganese dioxide in 50 ml toluene is heated to reflux for 1 hr. and filtered through a pad of silica gel. Evaporation of the solvent yields 3.5 g (88%) of yellow crystalline solids.

M.P.: 98°–101° C. Calcd. exact mass: 302.15448; Obsd. exact mass: 302.15404. NMR(90 MH$_z$): α1.4,d,6H; 3.5,m,1H; 5.9,d,1H; 6.1,d,1H; 7.1–77,m,8H; 8.1,d,1H; 9.5,d,1H.

Step G: Preparation of 6-Heptenoic acid, 5-hydroxy-7-[2-(2-methylethyl)-4-phenylquinolin-3-yl]-3-oxoethyl ester, (E)-

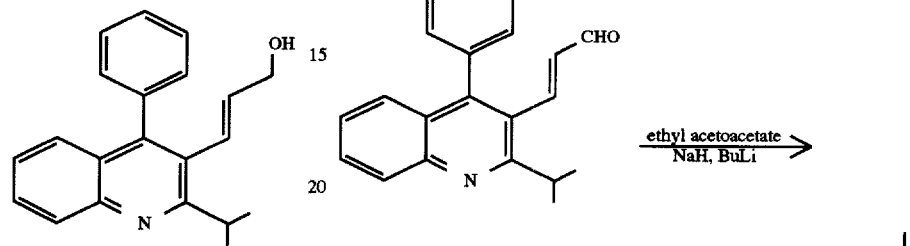

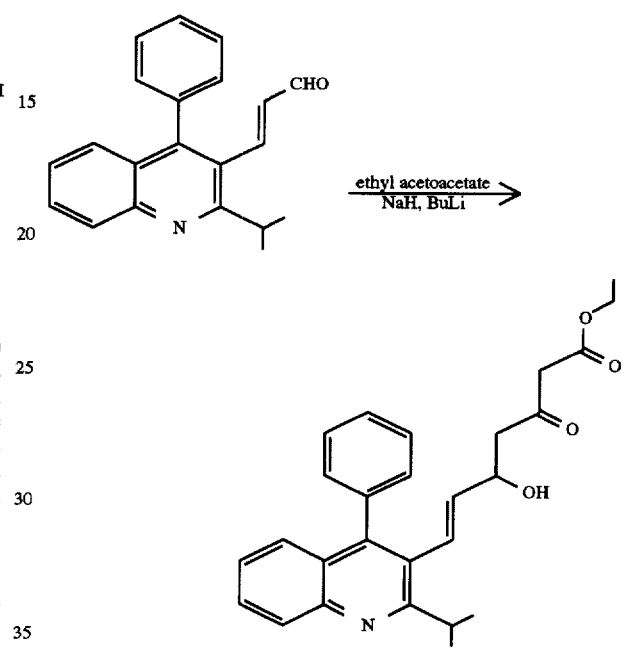

To a solution of 5 ml (0.04 mole) ethyl acetoacetate in 50 ml dry THF is added at −5° to −10° C., 1.9 g 50% NaH in mineral oil. After stirring for 15 min. at this temperature, 27 ml. 1.6M BuLi/hex. is added at −10° to −13° C. Continued stirring at −10° C. for 20 min. gives 92 ml (0.04 mole) of dianion of ethyl acetoacetate as a yellow homogeneous solution.

To a solution of 3.5 g (0.0116 mole) of α,β-unsaturated quinoline aldehyde in 40 ml dry THF is added at −5° to −10° C. 38 ml (0.0165 mole, 1.2 equiv.) of the above dianion solution, freshly prepared. After ½ hr. stirring at this temperature, the reaction mixture is quenched with saturated NH$_4$Cl, extracted with ethyl acetate and washed with water and brine. The ethyl acetate layer is dried over anhydrous MgSO$_4$ and concentrated in vacuo. The crude product is chromatographed on silica gel. Elution with 25% ether/pet. ether gives 3.4 g. (67.8%) α,β-unsaturated hydroxy keto ester as yellow solids.

M.P.: 84°–87° C. Anal. Calcd. for C$_{27}$H$_{29}$NO$_4$: C, 75.15; H, 677; N, 3.25. Found: C, 74.99; H, 7.04; N, 2.98. NMR (200 MH$_z$,CDCl$_3$): α1.3,t,3H; 1.35, pair of d,6H; 2.3,m,2H; 2.5,d,1H; 3.35,s,1H; 3.5,m,1H; 4.2,q,2H; 4.5, broad s,1H; 5.25,q,1H; 6.55,d,1H; 7.1–7.7,m,8H; 8.1,d,1H.

Step H: Preparation of 6-Heptenoic acid, 3,5-dihydroxy-7-[2-(1-methylethyl)-4-phenylquinolin-3-yl]-ethyl ester, (±)-(E)-

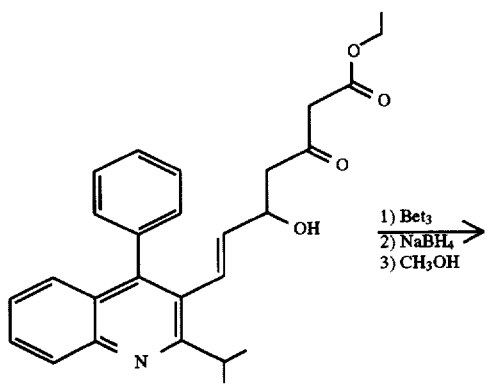

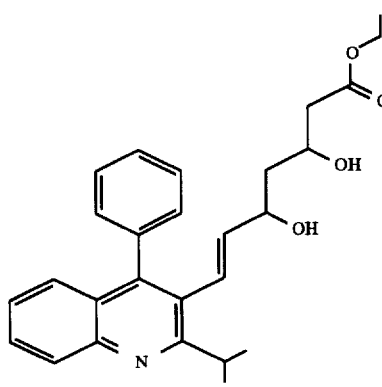

A solution of 1.0 g (0.0023201 mole) hydroxy keto ester and 3.5 ml (0.0034801 mole) 1M Et₃B/THF in 2.5 ml/10 ml MeOH/THF is stirred at R.T. for 1 hr. Then, 0.1315 g (0.0034801 mole) NaBH₄ is added at −78° C. portionwise. After stirring for 4 hrs. at −78° C., 5 ml acetic acid is added, followed by the addition of ethyl acetate at R.T. The ethyl acetate extracts are combined, washed with saturated sodium bicarbonate, water, and brine and are dried over anhydrous MgSO₄. Removal of solvent in vacuo yields a crude product which is redissolved in methanol and concentrated. This procedure is repeated until a boron complex disappears from a thin layer chromatograph (using 50% ether/petroleum ether) and only main product appears. The crude product (1.0914 g), an orange oil, is chromatographed on silica gel. Elution with 80% ether/pet. ether gives 0.91 g (90.5%) yellow solids.

M.P.: 104°–106° C. NMR (200 MH$_z$,CDCl₃): δ1.3,t,3H; 1.35,d,6H; 2.35,m,1H; 2.9,d,1H; 3.6,d,1H; 3.5,m,1H; 4.0,m, 1H; 4.2,q,2H; 4.35,m,1H; 5.35,q,1H; 6.6,d,1H; 7.1–7.7,m, 8H; 8.1,d,1H.

EXAMPLE 2

Step A: Preparation of Acetamide, N-[2-(3,5-dimethylbenzoyl)phenyl]-

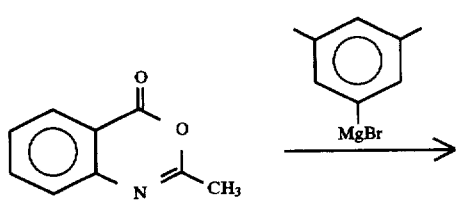

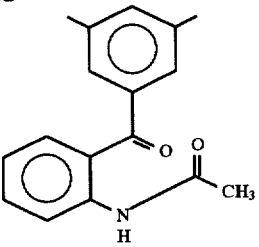

4H-3,1-benzoxazine-4-one, 2-methyl- is prepared according to Morrison and Mullholland, 1958, *J. Chem. Soc.* p. 2702, and 10 g (0.0621 mol) in THF (50 ml) is added dropwise to a solution of 3,5-dimethylphenyl-magnesium bromide (which is prepared from 17.2 g (0.0931 mole) 5-bromo-m-xylene, 2.33 g(0.0931 mole) magnesium, a trace of iodine, and 1,2-dibromoethan in 40 ml diethyl ether). The resultant mixture is stirred at room temperature under nitrogen, then quenched with a saturated ammonium chloride solution, and is extracted with ethyl acetate. The extracts are dried (Na₂SO₄) and evaporated at a reduced pressure. The resulting oil (10 g) is chromatographed on a silica gel column to obtain the product as an oil (6 g).

Step B: Preparation of Methanone, (2-aminophenyl)(3,5-dimethylphenyl)-hydrochloride

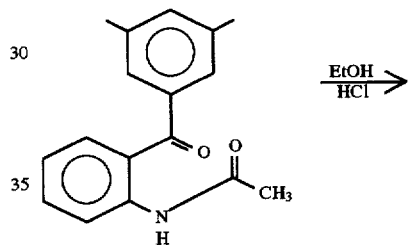

A mixture of the keto amide of Step A (3.8 g., 0.01428 mol) and 12N hydrochloric acid (1.19 ml, 0.01428 mol) in 20 ml absolute ethanol is stirred and is heated at reflux for 3 hrs. The mixture is then cooled and diluted with diethyl ether. The resulting solid is collected by filtration, washed with diethyl ether and vacuum dried to yield 2.85 g of a pale yellow solid, m.p. 193°–195° C.

Step C: Preparation of 3-Quinolinecarboxylic acid, 4-(3,5-dimethylphenyl)-2-methyl-methyl ester

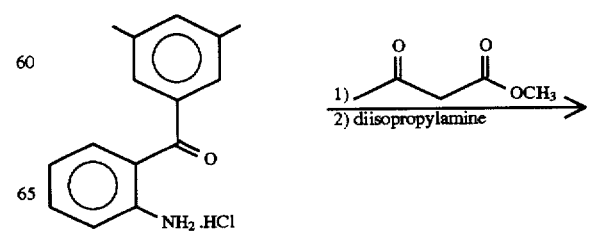

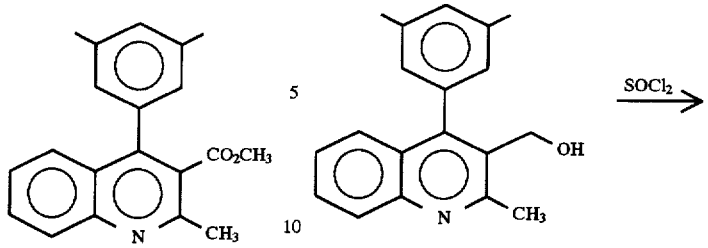

A mixture of the ketone hydrochloride of Step B (0.8 g, 0.003059 mol), and 0.33 ml., (0.00306 mol) methyl acetoacetate is stirred in 20 ml ethanol at reflux for 3 hrs. The mixture is slowly cooled to 10° C. and diluted with diethyl ether. The precipitating white solid is collected by filtration and dried to obtain 930 mg of the quinoline hydrochloride, m.p. 209°–211° C.

A mixture of 620 mg of the above hydrochloride salt and 2 ml diisopropylamine in 10 ml dry diethylether is stirred at room temperature for 1 hr. The mixture is diluted with diethyl ether, and the diisopropylamine hydrochloride is removed by filtration. The remaining filtrate is evaporated at reduced pressure, and a colorless oil results. The product, a colorless solid, is crystallized from petroleum ether. Yield is 600 mg., m.p. 88°–90° C.

Step D: Preparation of 3-Quinolinemethanol, 4-(3,5-dimethylphenyl)-2-methyl-

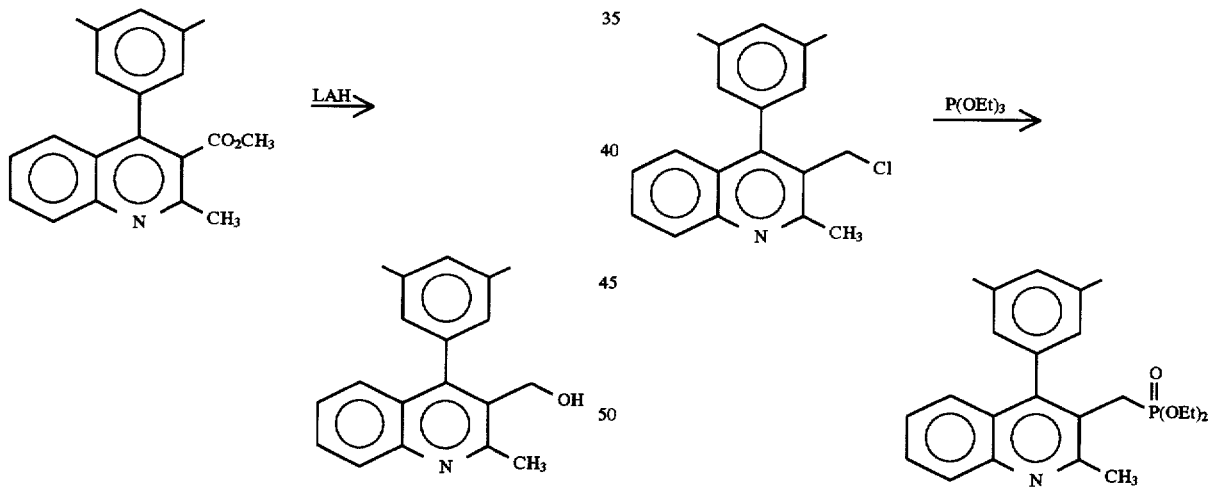

148 mg of lithium aluminum hydride is added to a solution of 486 mg (0.00189 mol) of the ester of Step C in 9 ml dry diethyl ether at 0° C., and stirred at 0° C. for 3.5 hrs. The reaction mixture is poured into cold water and extracted with ethyl acetate. The extracts are dried (Na$_2$SO$_4$) and are filtered. The filtrate is concentrated at a reduced pressure to give solids. This product is recrystallized in petroleum ether to yield 213 mg of a colorless solid, m.p. 194°–195° C.

Step E: Preparation of Quinoline, 3-chloromethyl-4-(3,5-dimethylphenyl)-2-methyl- 0.1 ml (0.00137 mol) thionyl chloride is added to a solution of 190 mg (0.0006859 mol) of the quinoline alcohol of Step D in 5 ml CH$_2$Cl$_2$ at room temperature. This solution is stirred at room temperature for 4 hours, after which the solvent is removed at reduced pressure. The resulting oil is purified by Prep TLC (ether-petroleum 1:1) to yield 160 mg of a white solid.

Step F: Preparation of Phosphonic acid [[4-(3,5-dimethylphenyl)-2-methylquinolin-3-yl]methyl]-diethyl ester 150 mg (0.000508 mol) of the chloride of Step E is mixed with 0.8 ml triethyl phosphite in 2 ml toluene, and then is stirred at reflux under nitrogen for 20 hours. The result is evaporated under reduced pressure to give an oily product which solidifies upon standing to yield 160 mg of product, m.p. 105°–107° C.

Step G: Preparation of 6-Heptenoic acid, 3,5-bis[[(1,1-dimethylethyl)diphenylsilyl]oxy]-7-[4-(3,5-dimethylphenyl)-2-methylquinolin-3-yl]-ethylester [(R*, S*)-(E)]-(+,−)-

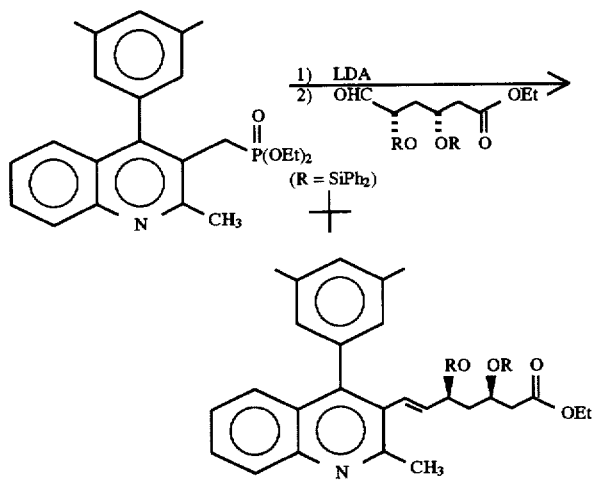

A solution of 0.27 ml (1.7M) lithium diisopropylamide monotetrahydrofuran/cyclohexane is added to 150 mg (0.000378 mol) of the diethyl phosphonate of Step F in 3 ml THF, at −55° C. The mixture is stirred at −55° to −60° C. for 10 min., then a solution of the above aldehyde (293 mg, 0.0004534 mol) in 2 ml THF is added dropwise at −55° C. The reaction mixture is stirred at −55° C. for 20 min. Next, 0.5 ml acetic acid and 10% HCl are added, and the mixture is extracted with ethyl acetate. The extracts are combined, washed with water, saturated sodium bicarbonate, water, and brine, then dried ($Na_2SO_4$), filtered, and evaporated at a reduced pressure to give the crude product as a yellow oil. Preparative TLC (ether:petroleum 1:1) yields 100 mg of a pale yellow oil.

Step H: Preparation of 6-Heptenoic acid, 7-[4-(3,5-dimethylphenyl)-2-methylquinolin-3-yl]-3,5-dihydroxy-ethyl ester [(R*,S*)-(E)]-, (+,−)- and 2H-Pyran-2-one, 6-[2-[4-(3,5-dimethylphenyl)-2-methylquinolin-3-yl]-ethenyl] tetrahydro[trans-(E)]-, (+,−)-

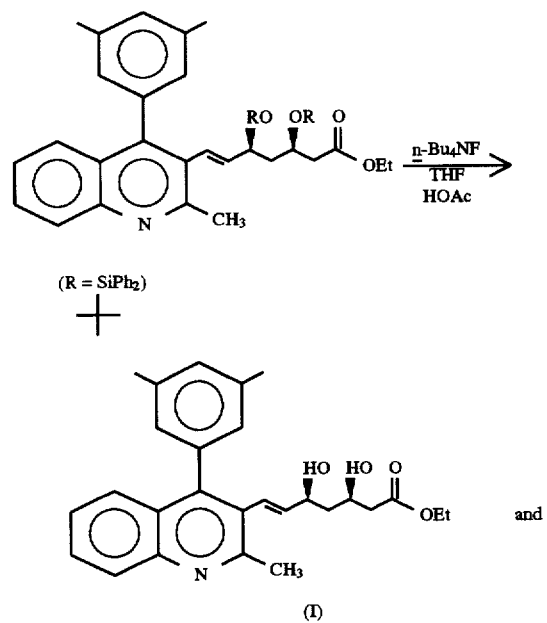

To a solution of the silyl ether of Step G (90 mg, 0.0001012 mol) and glacial acetic acid (0.03 ml, 0.0005 mol) in 2 ml THF at room temperature is added a solution of 1M, 0.61 ml, 0.000607 mol of tetra-n-butyl ammonium fluoride/tetrahydrofuran. The reaction mixture is stirred at 50°–60° C. for 40 hr. The mixture is then evaporated at a reduced pressure to give the crude product as a brown oil. This is purified by preparative chromatography (ether:ethyl acetate 1:1) to obtain product I as an oil (10 mg) and product II as an oil (10 mg).

The Formula I compound is in an erythro:threo ratio of approximately 95:5. Nmr analysis yields the following:

1.3 (t, 3H); 2.4 (m, 5H); 4.1 (m, 1H); 4.2 (q, 2H); 4.4 (m, 1H); 5.5 (q, 1H); 6.5 (d, 1H); 6.7–8 (m, 7H).

The Formula II compound is in a cis:trans ratio of approximately 5:95. Nmr analysis yields the following:

2.3 (s, 1H); 2.5–2.9 (m, 4H); 4.1 (m, 1H); 5.1 (m, 1H); 5.5 (q, 1H); 6.6 (d, 1H); 6.8–8.0 (m, 7H).

EXAMPLE 3

Following procedures analogous to those described in Examples 1 and 4 the following compounds are made:

Example 3A

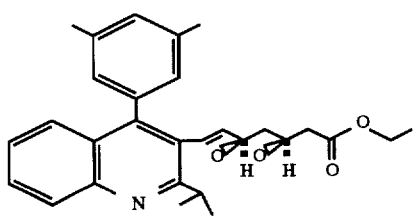

Example 3B

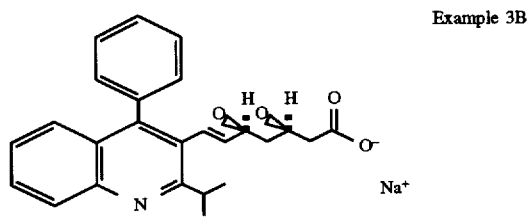

Example 3C

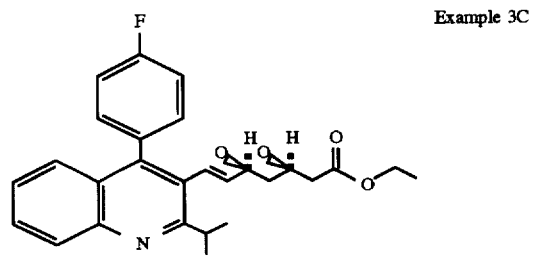

-continued

Example 3D

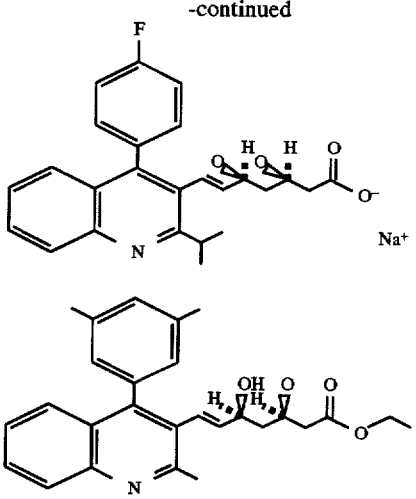

Example 3E

NMR analysis of the above compounds gives the following results:
Ex NMR spectra
3A 0.9 (t, 3H); 1.6 (d, 6H); 2.1 (m, 2H); 3.7 (m, 1H); 3.7–4.0 (m, 3H); 4.2 (m, 1H); 5.4 (q, 1H); 6.6–7.7 (m, 8H); 8.4 (d, 1H)
3B 1.4 (d, 6H); 2.2 (m, 2H); 3.6 (m, 1H); 3.8 (m, 1H); 4.2 (m, 1H); 5.4 (q, 1H); 6.6 (d, 1H); 7.1–7.7 (m, 8H); 8.1 (d, 1H)
3C 1.3 (t, 3H); 1.4 (dd, 6H); 2.4 (m, 2H); 3.1 (d, 1H); 3.5 (m, 1H); 3.6 (m, 1H); 4.1 (m, 1H); 4.2 (q, 2H); 4.4 (m, 1H); 5.4 (q, 1H); 6.6 (d, 1H); 7.0–7.4 (m, 7H); 7.6 (m, 1H); 8.1 (d, 1H)
3D 1.3 (d, 6H); 2.2 (m, 2H); 3.6 (m, 1H); 3.8 (m, 1H); 4.25 (m, 1H); 5.5 (q, 1H); 6.6 (d, 1H); 7.3–7.4 (m, 7H); 7.6 (m, 1H); 8.1 (d, 1H)
3E 1.3 (t, 3H); 2.4 (m, 5H); 4.1 (m, 1H); 4.2 (q, 2H); 4.4 (m, 1H); 5.5 (q, 1H); 6.5 (d, 1H); 6.7–8 (m, 7H)

d=doublet; dd=doublet of a doublet;
m=multiplet; q=quartet, t=triplet

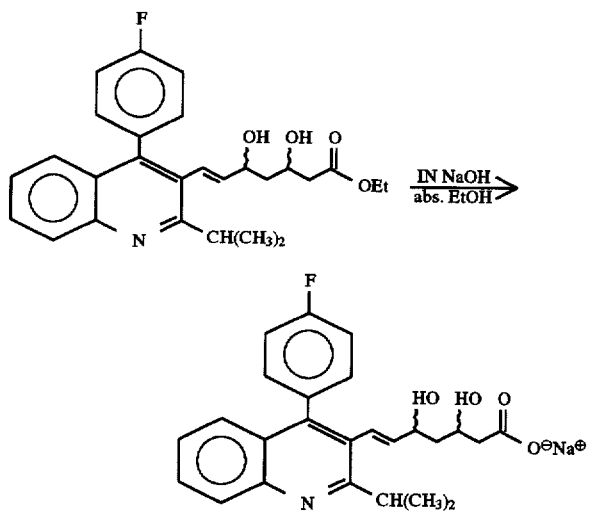

To a solution of 100 mg (0.00022172 mole) of the diol ester of Example 1 in 3 ml absolute ethanol is added 0.2173 ml (0.000217294 mole) 1N NaOH dropwise at 0° C. The mixture is stirred for 3 hours at 0° C., then diluted with ether and is evaporated in vacuo, leaving a yellow oil. Upon the addition of ether, yellow solids are precipitated out, which are then filtered, washed with ether and dried (86.4 mg), m.p.>225° C.

NMR (CD$_3$OD, 500 MH$_2$): 1.39 (m, 1H); 1.35 (d, 6H); 1.5 (m, 1H); 2.13–2.3 (m, 1H); 3.65 (q, 1H); 3.75 (m, 1H); 4.25 (m, 1H); 5.45 (dd, 1H); 6.59 (d, 1H); 7.21 (m, 5H); 7.36 (m, 1H); 7.62 (m, 1H); 8.05 (d, 1H).

What is claimed is:

1. A compound of the formula

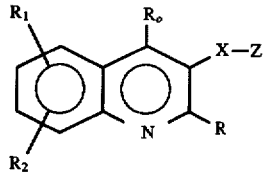

wherein each of R and R$_o$ is, independently, C$_{1-6}$alkyl, C$_{3-7}$cycloalkyl or

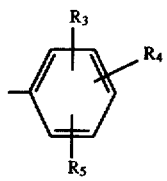

each of R$_1$, R$_2$, R$_3$, R$_4$ and R$_5$ is, independently, hydrogen, C$_{1-4}$alkyl, C$_{1-4}$alkoxy, trifluoromethyl, fluoro, chloro, phenoxy, benzyloxy or hydroxy;

with the provisos that not more than one of R$_1$ and R$_2$ is trifluoromethyl, not more than one of R$_1$ and R$_2$ is phenoxy, not more than one of R$_1$ and R$_2$ is benzyloxy, not more than one of R$_1$ and R$_2$ is hydroxy, not more than one of R$_3$–R$_5$ is trifluoromethyl, not more than one of R$_3$–R$_5$ is phenoxy, not more than one of R$_3$–R$_5$ is benzyloxy, and not more than one of R$_3$–R$_5$ is hydroxy;

X is —(CH$_2$)$_2$— or —CH=CH—;

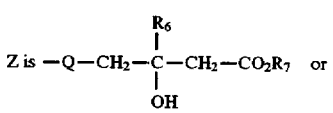 (a)

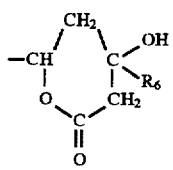 (b)

wherein Q is —C— or —CH—;
            ‖          |
            O          OH with the proviso that Q may be

only when X is —CH=CH—
or R$_6$ is C$_{1-3}$alkyl or both,

R$_6$ is hydrogen or C$_{1-3}$alkyl;

R$_7$ is hydrogen, R$_8$ or M;

R$_8$ is a physiologically acceptable and hydrolyzable ester group; and

M is a pharmaceutically acceptable cation.

2. A compound according to claim 1 wherein Z is (a) and Q is

3. A compound according to claim 2 which is a 3R,5S isomer.

4. A compound according to claim 2 wherein R and $R_o$ are independently $CH_3$, isopropyl, phenyl, 3,5-dimethylphenyl or 4-fluorophenyl.

5. A compound according to claim 1 which is (E,)-6-heptenoic acid, 3,5-dihydroxy-7-[2-(1-methylethyl)-4-phenylquinolin-3-yl]-ethyl ester, or its sodium salt.

6. A compound according to claim 1 which is 7-[4-(3,5-dimethylphenyl)-2-methylquinolin-3-yl-3,5-dihydroxy-ethyl ester, or its sodium salt.

7. A compound according to claim 1 which is 6-[2-[4-(3,5-dimethylphenyl)-2-methylquinolin-3-yl]-ethenyl] tetrahydro-2H-pyran-2-one, or its sodium salt.

8. A method of inhibiting cholesterol biosynthesis comprising administering to a mammal in need of such treatment a cholesterol-biosynthesis-inhibiting amount of a compound of claim 1.

9. A method of treating atherosclerosis comprising administering to a mammal in need of such treatment an effective amount of a compound according to claim 1, said effective amount being an amount effective for the treatment of atherosclerosis.

10. A pharmaceutical composition comprising a cholesterol-biosynthesis inhibiting amount of a compound according to claim 1 and a pharmaceutically acceptable carrier.

* * * * *

UNITED STATES PATENT AND TRADEMARK OFFICE
CERTIFICATE OF CORRECTION

PATENT NO. : 5,753,675
DATED : May 19, 1998
INVENTOR(S) : Sompong Wattanasin

It is certified that error appears in the above-identified patent and that said Letters Patent is hereby corrected as shown below:

Claim 1 (column 34, line 60) change "-CH=CH" to -CH=CH-.

Claim 5, line 1, remove the comma following "E".

Signed and Sealed this

First Day of September, 1998

Attest:

BRUCE LEHMAN

Attesting Officer

Commissioner of Patents and Trademarks